(12) United States Patent
Wang et al.

(10) Patent No.: US 8,727,203 B2
(45) Date of Patent: May 20, 2014

(54) METHODS FOR MANUFACTURING POROUS ORTHOPAEDIC IMPLANTS

(75) Inventors: Aiguo Wang, Wayne, NJ (US); Daniel E. Lawrynowicz, Monroe, NY (US); Haitong Zeng, Oakland, NJ (US); Naomi Murray, Yorktown Heights, NY (US); Balaji Prabhu, Upper Saddle River, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 265 days.

(21) Appl. No.: 12/883,447

(22) Filed: Sep. 16, 2010

(65) Prior Publication Data

US 2012/0067853 A1   Mar. 22, 2012

(51) Int. Cl.
*B23K 20/02* (2006.01)
*B23K 26/00* (2014.01)

(52) U.S. Cl.
USPC ........... 228/193; 228/249; 228/253; 428/655; 428/660

(58) Field of Classification Search
CPC ..................................................... B23K 20/02
USPC ............... 228/193, 194, 249, 253; 623/13.11, 623/16.11; 428/650–668
See application file for complete search history.

(56) References Cited

U.S. PATENT DOCUMENTS

| | | | |
|---|---|---|---|
| 1,886,615 A | 11/1932 | Johnson | |
| 2,133,292 A | 10/1938 | Gordon | |
| 2,505,896 A | 5/1950 | Hedlund | |
| 2,745,172 A | 5/1956 | Townsend | |
| 3,015,885 A | 1/1962 | McEuen et al. | |
| 3,061,912 A | 11/1962 | Kalil | |
| 3,070,880 A | 1/1963 | Davis et al. | |
| 3,168,782 A | 2/1965 | Cochran | |
| 3,173,202 A | 3/1965 | Farber | |
| 3,222,774 A | 12/1965 | Kump et al. | |
| 3,299,503 A | 1/1967 | Freyberger et al. | |
| 3,605,123 A | 9/1971 | Pratt et al. | |
| 3,608,490 A | 9/1971 | O'Keefe | |

(Continued)

FOREIGN PATENT DOCUMENTS

| DE | 3910603 A1 | 10/1990 |
|---|---|---|
| EP | 1035230 A1 | 9/2000 |

(Continued)

OTHER PUBLICATIONS

Ashworth, Materials and Design, 21, 351-358, 2000.

*Primary Examiner* — Devang R Patel
(74) *Attorney, Agent, or Firm* — Lerner, David, Littenberg, Krumholz & Mentlik, LLP

(57) ABSTRACT

A method of manufacturing an orthopaedic implant device having a porous outer surface is described. In one embodiment, the implant device includes a porous layer, an intermediate layer, and a solid substrate. The porous layer is preferably bonded to the intermediate layer by cold isostatic pressing. The intermediate layer is preferably bonded by vacuum welding to the solid substrate such that the porous layer forms at least a portion of the outer surface of the orthopaedic implant device. Preferably, a diffusion bond is created between the bonded intermediate layer and the solid substrate by hot isostatic pressing. In another embodiment, a porous layer is created on an outer surface of a solid layer by selective melting. Preferably, the solid layer is bonded to the solid substrate such that the porous layer forms at least a portion of the outer surface of the orthopaedic implant device.

14 Claims, 7 Drawing Sheets

(56) References Cited

U.S. PATENT DOCUMENTS

| | | |
|---|---|---|
| 3,762,032 A | 10/1973 | Bowling et al. |
| 3,798,748 A | 3/1974 | Holko |
| 3,808,606 A | 5/1974 | Tronzo |
| 3,834,001 A | 9/1974 | Carroll et al. |
| 3,835,514 A | 9/1974 | Pollack |
| 3,855,638 A | 12/1974 | Pilliar |
| 3,889,349 A | 6/1975 | Kaufman |
| 3,906,550 A | 9/1975 | Rostoker et al. |
| 3,984,043 A | 10/1976 | Kreider et al. |
| 3,985,283 A | 10/1976 | Gempler |
| 3,996,019 A | 12/1976 | Cogan |
| 3,999,699 A | 12/1976 | Chisholm |
| 4,008,844 A | 2/1977 | Duvall et al. |
| 4,024,617 A | 5/1977 | McCormick |
| 4,033,504 A | 7/1977 | Fletcher et al. |
| 4,042,162 A | 8/1977 | Meginnis et al. |
| 4,046,302 A | 9/1977 | Schladitz |
| 4,065,046 A | 12/1977 | Roberts et al. |
| 4,071,183 A | 1/1978 | Cogan |
| 4,073,999 A | 2/1978 | Bryan et al. |
| 4,114,794 A | 9/1978 | Storms |
| 4,150,776 A | 4/1979 | Lesgourgues |
| 4,152,816 A | 5/1979 | Ewing et al. |
| 4,156,943 A | 6/1979 | Collier |
| 4,179,485 A | 12/1979 | Tritten |
| 4,183,456 A | 1/1980 | Schilling et al. |
| 4,218,007 A | 8/1980 | Schilling et al. |
| 4,245,769 A | 1/1981 | Meginnis |
| 4,362,582 A | 12/1982 | Danko |
| 4,469,757 A | 9/1984 | Ghosh et al. |
| 4,479,271 A | 10/1984 | Bolesky et al. |
| 4,485,961 A | 12/1984 | Ekbom et al. |
| 4,529,452 A | 7/1985 | Walker |
| 4,570,271 A | 2/1986 | Sump |
| 4,581,300 A | 4/1986 | Hoppin, III et al. |
| 4,594,219 A | 6/1986 | Hostatter et al. |
| 4,601,087 A | 7/1986 | Kawai et al. |
| 4,603,801 A | 8/1986 | Wan et al. |
| 4,604,780 A | 8/1986 | Metcalfe |
| 4,614,296 A | 9/1986 | Lesgourgues |
| 4,636,219 A | 1/1987 | Pratt et al. |
| 4,644,942 A | 2/1987 | Sump |
| 4,650,109 A | 3/1987 | Crivella et al. |
| 4,660,755 A | 4/1987 | Farling et al. |
| 4,673,124 A | 6/1987 | Conolly |
| 4,676,843 A | 6/1987 | Nazmy |
| 4,690,320 A | 9/1987 | Morishita et al. |
| 4,691,857 A | 9/1987 | Friedman |
| 4,695,699 A | 9/1987 | Yagii et al. |
| 4,700,881 A | 10/1987 | Ryan |
| 4,700,882 A | 10/1987 | Devine, Jr. |
| 4,710,235 A | 12/1987 | Scruggs |
| 4,724,120 A | 2/1988 | Bienvenu et al. |
| 4,746,055 A | 5/1988 | Ingram et al. |
| 4,763,828 A | 8/1988 | Fukaya et al. |
| 4,768,700 A | 9/1988 | Chen |
| 4,805,833 A | 2/1989 | Seimers |
| 4,811,892 A | 3/1989 | Kunzmann et al. |
| 4,813,965 A | 3/1989 | Roberts |
| 4,846,393 A | 7/1989 | Devillard |
| 4,847,044 A | 7/1989 | Ghosh |
| 4,854,496 A | 8/1989 | Bugle |
| 4,934,581 A | 6/1990 | Ibe et al. |
| 4,940,180 A | 7/1990 | Martell |
| 4,969,907 A | 11/1990 | Koch et al. |
| 4,982,893 A | 1/1991 | Ruckle et al. |
| 4,995,548 A | 2/1991 | Wang et al. |
| 5,000,371 A | 3/1991 | Johnson |
| 5,009,359 A | 4/1991 | Stover et al. |
| 5,024,368 A | 6/1991 | Bottomley et al. |
| 5,027,998 A | 7/1991 | Bugle |
| 5,034,186 A | 7/1991 | Shimamune et al. |
| 5,069,383 A | 12/1991 | Cooper et al. |
| 5,080,674 A | 1/1992 | Jacobs et al. |
| 5,100,050 A | 3/1992 | Krueger et al. |
| 5,106,012 A | 4/1992 | Hyzak et al. |
| 5,141,145 A | 8/1992 | Das et al. |
| 5,163,604 A | 11/1992 | Moe |
| 5,165,591 A | 11/1992 | Pratt |
| 5,192,324 A | 3/1993 | Kenna |
| 5,215,243 A | 6/1993 | Findlan |
| 5,224,645 A | 7/1993 | Cooper et al. |
| 5,226,578 A | 7/1993 | Douglas |
| 5,236,116 A | 8/1993 | Solanki et al. |
| 5,253,794 A | 10/1993 | Siemers et al. |
| 5,258,030 A | 11/1993 | Wolfarth et al. |
| 5,271,776 A | 12/1993 | Siemers et al. |
| 5,297,723 A | 3/1994 | Benn et al. |
| 5,323,954 A | 6/1994 | Shetty et al. |
| 5,326,525 A | 7/1994 | Ghosh |
| 5,330,097 A | 7/1994 | Inoue |
| 5,405,389 A | 4/1995 | Conta et al. |
| 5,441,537 A | 8/1995 | Kenna |
| 5,464,440 A | 11/1995 | Johansson |
| 5,487,933 A | 1/1996 | White |
| 5,489,306 A | 2/1996 | Gorski |
| 5,504,300 A | 4/1996 | Devanathan et al. |
| 5,544,805 A | 8/1996 | Alassoeur et al. |
| 5,562,245 A | 10/1996 | Berthelemy et al. |
| 5,564,620 A | 10/1996 | Rawers et al. |
| 5,578,148 A | 11/1996 | Eylon et al. |
| 5,593,085 A | 1/1997 | Tohill et al. |
| 5,607,778 A | 3/1997 | Padden |
| 5,624,516 A | 4/1997 | Hanusiak et al. |
| 5,650,108 A | 7/1997 | Nies et al. |
| 5,702,446 A | 12/1997 | Schenck et al. |
| 5,734,959 A | 3/1998 | Krebs et al. |
| 5,773,789 A | 6/1998 | Devanathan et al. |
| 5,807,443 A | 9/1998 | Masuda et al. |
| 5,812,925 A | 9/1998 | Ecer |
| 5,863,398 A | 1/1999 | Kardokus et al. |
| 5,893,511 A | 4/1999 | Schwarzbauer |
| 5,947,893 A | 9/1999 | Agrawal et al. |
| 6,005,164 A | 12/1999 | Johansson et al. |
| 6,036,081 A | 3/2000 | Gruber |
| 6,049,054 A | 4/2000 | Panchison et al. |
| 6,049,978 A | 4/2000 | Arnold |
| 6,060,640 A | 5/2000 | Pauley et al. |
| 6,085,965 A | 7/2000 | Schwartz et al. |
| 6,085,966 A | 7/2000 | Shimomuki et al. |
| 6,087,553 A | 7/2000 | Cohen et al. |
| 6,096,212 A | 8/2000 | Quick et al. |
| 6,129,993 A | 10/2000 | Kumamoto et al. |
| 6,164,524 A | 12/2000 | Iwadachi |
| 6,168,072 B1 | 1/2001 | Schwartz et al. |
| 6,193,761 B1 | 2/2001 | Treacy |
| 6,214,134 B1 | 4/2001 | Eylon et al. |
| 6,222,150 B1 | 4/2001 | Nomura et al. |
| 6,248,290 B1 | 6/2001 | Kuwabara |
| 6,264,095 B1 | 7/2001 | Stouffer et al. |
| 6,312,473 B1 | 11/2001 | Oshida |
| 6,315,798 B1 | 11/2001 | Ashby et al. |
| 6,323,458 B1 | 11/2001 | Nomura et al. |
| 6,326,088 B1 | 12/2001 | Mayer et al. |
| 6,328,198 B1 | 12/2001 | Ohashi et al. |
| 6,331,214 B1 | 12/2001 | Koga et al. |
| 6,364,971 B1 | 4/2002 | Peterson, Jr. et al. |
| 6,378,760 B1 | 4/2002 | Shimizu et al. |
| 6,447,550 B1 | 9/2002 | Hunter et al. |
| 6,454,811 B1 | 9/2002 | Sherwood et al. |
| 6,464,129 B2 | 10/2002 | Stueber et al. |
| 6,485,521 B1 | 11/2002 | Say et al. |
| 6,552,292 B1 | 4/2003 | Nomura et al. |
| 6,579,431 B1 | 6/2003 | Bolcavage et al. |
| 6,582,470 B1 | 6/2003 | Lee et al. |
| 6,599,322 B1 | 7/2003 | Amrich et al. |
| 6,619,537 B1 | 9/2003 | Zhang et al. |
| 6,704,988 B2 | 3/2004 | Kenney et al. |
| 6,726,725 B2 | 4/2004 | Hunter et al. |
| 6,797,006 B2 | 9/2004 | Hodorek |
| 6,810,572 B2 | 11/2004 | Kistner et al. |
| 6,840,432 B1 | 1/2005 | Ramarge et al. |
| 6,857,558 B2 | 2/2005 | Ferry, III et al. |
| 6,863,209 B2 | 3/2005 | Rinne et al. |

(56) References Cited

U.S. PATENT DOCUMENTS

| | | |
|---|---|---|
| 6,913,623 B1 | 7/2005 | Zhu |
| 6,955,288 B2 | 10/2005 | Barnes et al. |
| 7,043,819 B1 | 5/2006 | Arnold |
| 7,048,870 B1 | 5/2006 | Ellingsen et al. |
| 7,087,085 B2 | 8/2006 | Steinemann et al. |
| 7,291,178 B2 | 11/2007 | Sul |
| 7,431,197 B2 | 10/2008 | Franchet et al. |
| 7,431,734 B2 | 10/2008 | Danoff et al. |
| 7,458,991 B2 | 12/2008 | Wang et al. |
| 7,473,278 B2 | 1/2009 | Hunter et al. |
| 7,484,651 B2 | 2/2009 | Gandy et al. |
| 7,497,876 B2 | 3/2009 | Tuke et al. |
| 7,501,073 B2 | 3/2009 | Wen et al. |
| 7,516,529 B2 | 4/2009 | Morales et al. |
| 7,582,118 B2 | 9/2009 | Brown et al. |
| 7,597,715 B2 | 10/2009 | Brown et al. |
| 2001/0004711 A1 | 6/2001 | Lazzara et al. |
| 2001/0023371 A1 | 9/2001 | Bonutti |
| 2002/0016635 A1 | 2/2002 | Despres et al. |
| 2002/0104875 A1 | 8/2002 | Stueber et al. |
| 2002/0106611 A1 | 8/2002 | Bhaduri et al. |
| 2002/0126573 A1 | 9/2002 | Schubert et al. |
| 2002/0148880 A1 | 10/2002 | Brink |
| 2002/0151983 A1 | 10/2002 | Shetty |
| 2002/0153348 A1 | 10/2002 | Say et al. |
| 2002/0198601 A1 | 12/2002 | Bales et al. |
| 2003/0033020 A1 | 2/2003 | Hunter et al. |
| 2003/0033022 A1 | 2/2003 | Plouhar et al. |
| 2003/0045941 A1 | 3/2003 | Lewallen |
| 2003/0055505 A1 | 3/2003 | Sicotte et al. |
| 2003/0065401 A1 | 4/2003 | Amrich et al. |
| 2003/0088980 A1 | 5/2003 | Arnold |
| 2003/0135282 A1 | 7/2003 | Anitua |
| 2003/0171820 A1 | 9/2003 | Wilshaw et al. |
| 2003/0176927 A1 | 9/2003 | Steinemann et al. |
| 2003/0220696 A1 | 11/2003 | Levine et al. |
| 2004/0054417 A1 | 3/2004 | Soffiati et al. |
| 2004/0078086 A1 | 4/2004 | Gunther |
| 2004/0081572 A1 | 4/2004 | Bampton et al. |
| 2004/0133283 A1 | 7/2004 | Shetty |
| 2004/0148026 A1 | 7/2004 | Bonutti |
| 2004/0167632 A1 | 8/2004 | Wen et al. |
| 2004/0167633 A1 | 8/2004 | Wen et al. |
| 2004/0232211 A1 | 11/2004 | Kayser et al. |
| 2004/0236338 A1 | 11/2004 | Hall |
| 2004/0243133 A1 | 12/2004 | Materna |
| 2004/0243237 A1 | 12/2004 | Unwin et al. |
| 2005/0077341 A1 | 4/2005 | Larrieu et al. |
| 2005/0100578 A1 | 5/2005 | Schmid et al. |
| 2005/0123672 A1 | 6/2005 | Justin et al. |
| 2005/0143743 A1 | 6/2005 | Cigada et al. |
| 2005/0189401 A1 | 9/2005 | Butzer et al. |
| 2005/0242162 A1 | 11/2005 | Medlin et al. |
| 2006/0003179 A1 | 1/2006 | Wang et al. |
| 2006/0006212 A1 | 1/2006 | Thebault et al. |
| 2006/0045903 A1 | 3/2006 | Kadiyala et al. |
| 2006/0086776 A1 | 4/2006 | Gandy et al. |
| 2006/0122708 A1 | 6/2006 | Nakamura et al. |
| 2006/0138200 A1 | 6/2006 | Oehring et al. |
| 2006/0149391 A1 | 7/2006 | Opie et al. |
| 2006/0161263 A1 | 7/2006 | Sul |
| 2006/0229715 A1 | 10/2006 | Istephanous et al. |
| 2007/0154620 A1 | 7/2007 | Lawrynowicz et al. |
| 2007/0156249 A1* | 7/2007 | Lawrynowicz et al. ... 623/23.51 |
| 2007/0287027 A1 | 12/2007 | Justin et al. |
| 2007/0288021 A1* | 12/2007 | Rickels et al. .................. 606/69 |
| 2008/0116246 A1 | 5/2008 | Rigal et al. |
| 2008/0121263 A1 | 5/2008 | Schutte et al. |
| 2008/0161927 A1 | 7/2008 | Savage et al. |
| 2008/0190994 A1 | 8/2008 | Polvi et al. |
| 2008/0269893 A1 | 10/2008 | Bhatnagar et al. |
| 2008/0292898 A1 | 11/2008 | Straza |
| 2009/0072010 A1 | 3/2009 | Voice et al. |
| 2009/0093881 A1 | 4/2009 | Bandyopadhyay et al. |
| 2009/0098310 A1* | 4/2009 | Hippensteel et al. ......... 427/576 |
| 2009/0105843 A1 | 4/2009 | Purnell |

FOREIGN PATENT DOCUMENTS

| | | | |
|---|---|---|---|
| EP | 1433443 | A1 | 6/2004 |
| GB | 2027060 | A | 2/1980 |
| GB | 2142544 | A | 1/1985 |
| GB | 2154614 | A | 9/1985 |
| GB | 2250941 | A | 6/1992 |
| JP | 59050177 | A | 3/1984 |
| JP | 02142683 | A | 5/1990 |
| JP | 02169190 | A | 6/1990 |
| JP | 02247303 | A | 10/1990 |
| JP | 04009286 | A | 1/1992 |
| JP | 04022587 | A | 1/1992 |
| JP | 2009017904 | A | 1/2009 |
| WO | 9828458 | A1 | 7/1998 |

* cited by examiner

METHODS FOR MANUFACTURING POROUS ORTHOPAEDIC IMPLANTS

FIELD OF THE TECHNOLOGY

The present invention relates to methods for manufacturing orthopaedic implants, and in particular it relates to methods of bonding separate layers of material while protecting the material properties of the materials used in the manufacture of the orthopaedic implants.

BACKGROUND OF THE INVENTION

Orthopaedic implants are known to have at least a portion of an outer surface thereof be porous. A porous surface of an orthopaedic implant may be used in order to anchor the implant in place once it is implanted in the body. Preferably, a porous surface promotes ingrowth of surrounding bone tissue after implantation of an orthopaedic implant at a surgical site. Bone cement may also be introduced to the surgical site and enter the porous surface of an orthopedic implant to further anchor the implant in a preferred location and/or orientation.

Various manufacturing methods have been developed to create a porous surface for orthopaedic implants. The porosity of a porous surface may be manufactured based on the characteristics of the surrounding bone tissue at the surgical site or the viscosity of bone cement that may be applied to the implant. For instance, an implant having an outer surface with larger void spaces may be preferable for a bone cement having a higher viscosity because such a bone cement will have an easier time entering into the larger void spaces before solidifying.

In some applications, it is beneficial to have a porous surface with a particular configuration. Selective melting (SLM) using either a laser or electron beam can be used to create a porous surface having a pre-planned structure. During the SLM process, heat fusable powder is generally deposited one layer at a time into a container adapted to house the powder. For each layer, a moving energy beam is used to melt the powders in certain areas corresponding to the pre-planned geometry of a component being manufactured. In SLM, the energy beam is directed by a computer aided design (CAD) solid model of the component being fabricated. Layer by layer, the powders are gradually joined into a solid mass that forms a three-dimensional geometry. In areas not struck by the laser beam, the powders remain loose. The loose powders serve to support the solid regions of the component as the fabrication proceeds. At the completion of the process, the fabricated component may be removed from the container and the loose powders generally remain in the container.

Other methods of fabricating both porous and solid structures include traditional powder metallurgy (PM) processes. A typical PM process can include consolidation of powder with or without binding agents and/or soluble pore forming agents. The consolidated part is known as a "green" part, and can be shaped prior to subsequent processing steps. The subsequent processing steps can include removal of the pore forming agents and sintering.

For some manufacturing methods it is necessary to attach a fabricated porous structure to an implant that acts as a substrate for the porous structure. In order for a porous surface of an orthopaedic implant to function as desired once implanted, the structure of the porous surface should preferably be uncompromised. For example, maintaining the integrity of a porous surface is generally an important consideration in both the manufacture thereof and the bonding thereof to a substrate layer in the form of an orthopaedic implant. It is a further important consideration to bond a porous layer to a substrate layer without significantly negatively affecting the underlying mechanical properties of the substrate layer.

Sintering may cause material fragments, whether thermoplastic or metal, to fuse. In addition, any mechanical pressure used to hold the porous structure and substrate in intimate contact during sintering can also serve to deform and distort the porous structure. The resultant altered porosity of the orthopedic implant may inhibit the desired tissue ingrowth capability of the porous layer. Additionally, sinter bonding may rapidly degrade the mechanical properties of an underlying substrate due to either grain growth and/or phase transformation resulting in a change in grain and phase morphology. This issue is a particular problem for some forged or cast substrates. In particular for the titanium alloy Ti6Al4V, sinter bonding occurs above the Beta-transus, which may cause both a rapid increase in the beta grain size and a notable change in the shape of the alpha/beta distribution after cooling to room temperature. As a result of both, the fatigue properties of the Ti6Al4V may be significantly negatively affected. This limits the applications for which sinter bonding is appropriate to those with low fatigue requirements.

Traditional diffusion bonding of material layers generally requires heating of the layers to be bonded together and applying a force to the interface. Generally, the force is applied in a uniaxial or biaxial fashion and requires complex and specific fixturing for different component geometries (i.e. orthopaedic implants which may not be flat and/or uniplanar) and/or sizes with which to apply the uniaxial or biaxial forces. Such fixturing is generally specific to component size and/or geometry. In addition, traditional diffusion bonding generally applies force over a broad area on the outer surface of a porous layer. The pressure exerted on the outer surface of the porous layer generally needs to be limited in order to limit material deformation. The higher the pressures used during traditional diffusion bonding, the more deformation is caused.

There is therefore a need for a reliable and economical method to attach porous structures to substrates with a complex geometry.

BRIEF SUMMARY OF THE INVENTION

A first aspect of the present invention is a method of manufacturing an orthopaedic implant device having a porous outer surface comprising providing a porous layer, providing an intermediate layer, bonding the porous layer to the intermediate layer, providing a solid substrate in the form of an orthopedic implant device, and bonding the intermediate layer to the solid substrate such that the porous layer forms at least a portion of the outer surface of the orthopaedic implant device.

In one embodiment of the first aspect, the porous and intermediate layers and the solid substrate consist of titanium. In other embodiments, the porous and intermediate layers and/or the solid substrate is a titanium alloy such as Ti6Al4V.

Preferably, the porous layer has a first porosity, and both the intermediate layer and substrate layer are substantially non-porous.

In another embodiment of the first aspect, bonding the porous layer to the intermediate layer is performed by cold isostatic pressing (CIP). The CIP process is particularly applicable to PM articles in their green state.

Preferably, the bonding of the intermediate layer to the solid substrate is performed by vacuum welding. Preferably, after vacuum welding, a diffusion bond is created between the bonded intermediate layer and the solid substrate by hot isostatic pressing.

A second aspect of the present invention is a method of manufacturing an orthopaedic implant device having a porous outer surface comprising providing a solid layer having an outer surface and an inner surface, creating a porous layer on the outer surface of the solid layer by selective melting using a laser or electron beam, providing a solid substrate in the form of an orthopedic implant device having a surface and bonding the surface of the solid layer to the surface of the solid substrate such that the porous layer forms at least a portion of the surface of the orthopaedic implant device.

In one embodiment of the second aspect, the solid layer and solid substrate consist of titanium. In other embodiments, the solid layer and/or solid substrate is a titanium alloy such as Ti6Al4V.

Preferably, the porous layer has a first porosity and inner surface of the solid layer is substantially non-porous. Preferably, the solid substrate is substantially non-porous.

In another embodiment of the second aspect, bonding of the solid layer to the solid substrate is performed by vacuum welding. Preferably, a diffusion bond is created between the bonded solid layer and the solid substrate by hot isostatic pressing.

A third aspect of the present invention is a method of manufacturing an orthopaedic implant device having a porous outer surface comprising creating by selective melting using an energy beam a layer having a porous outer surface and a substantially non-porous inner surface, providing a solid substrate in the form of an orthopedic implant device having a surface, and bonding the inner surface of the layer to the surface of the solid substrate such that the porous outer surface of the layer forms at least a portion of the surface of the orthopaedic implant device.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
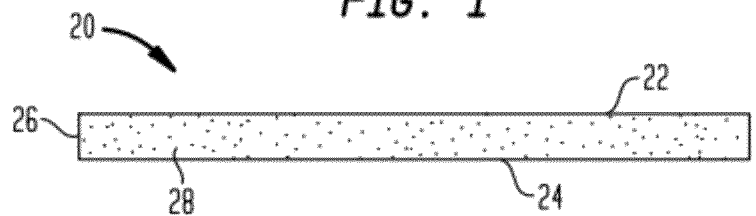
FIG. 1 is a side cross-sectional view of one embodiment of a porous layer.

Referring to FIGS. 1-5D, there is shown a representative of an implant device of the present invention designated generally by reference numeral 10. Implant device 10 includes a porous layer 20, an intermediate layer 30, and a solid substrate 40.

As shown in FIG. 1, porous layer 20 includes an outer surface 22 and an inner surface 24. Layer 20 has a thickness 26 preferably in the range of 1 mm to 10 mm and a porosity 28. The porosity 28 of porous layer 20 is based on the manufacturing process used in manufacturing layer 20. Layer 20 is made of a biocompatible material, preferably titanium, for example.

Layer 20 is shown in FIG. 1 as a plate-like structure. In other embodiment, layer 20 may have the structure of at least a portion of an outer surface of a corresponding orthopaedic implant, such as a femoral, tibial, or acetabular component, for example.

Other metallic powders and/or beads may be used to create porous layer 20 other than titanium powder. The amount of heat, pressure, and the length of time any material is processed in order to manufacture porous layer 20 are all examples of factors that may effect the porosity of porous layer 20. Further, the areas corresponding to the pre-planned geometry of manufacturing porous layer 20 effects the preferred porosity of layer 20.

Figure 2:
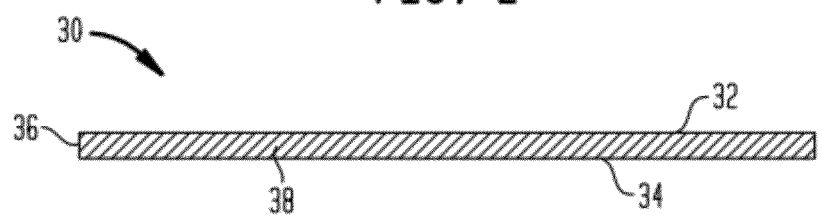
FIG. 2 is a side cross-sectional view of one embodiment of an intermediate layer.

As shown in FIG. 2, intermediate layer includes an outer surface 32 and an inner surface 34. Layer 30 has a thickness 36 and a porosity 38. Layer 30 is preferably made of titanium or a titanium alloy. Preferably, porosity 28 of porous layer 20 shown in FIG. 1 is higher than porosity 38 of intermediate layer 30 because porosity 38 is substantially non-porous. Preferably, intermediate layer 30 is a dense layer having substantially no porosity.

Figure 3A:
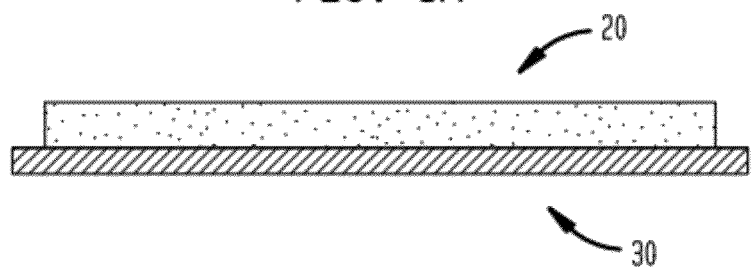
FIG. 3A is a side cross-sectional view of the porous layer shown in FIG. 1 bonded to the intermediate layer shown in FIG. 2.
Figure 3B:
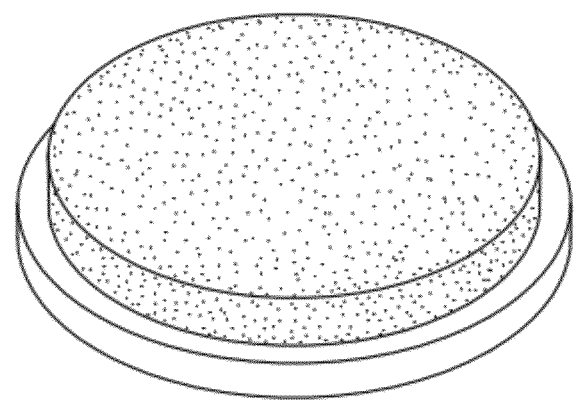
FIG. 3B is an isometric view of a structure having the bonded porous and intermediate layers shown in FIG. 3A.

FIGS. 3A and 3B shows inner surface 24 of porous layer 20 bonded to outer surface 32 of intermediate layer 30. In the preferred embodiment, porous layer 20 is bonded to intermediate layer 30 by cold isostatic pressing. Cold isostatic pressing applies pressure to porous layer 20 from multiple directions in order to achieve uniformity of compaction with intermediate layer 30.

Figure 4:
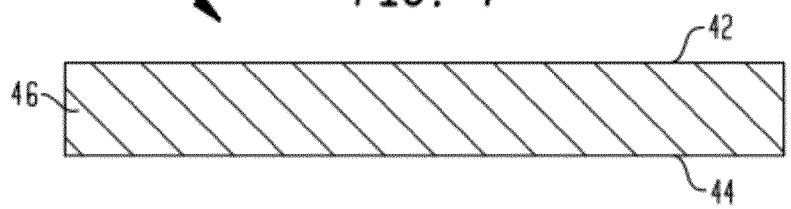
FIG. 4 is a side cross-sectional view of one embodiment of a solid substrate.

As shown in FIG. 4, solid substrate 40 includes an outer surface 42 and an inner surface 44. Solid substrate 40 includes a thickness 46. Solid substrate 40 is preferably titanium or a titanium alloy such as Ti6Al4V. Preferably, solid substrate 40 is a solid layer that is substantially non-porous.

Figure 5A:
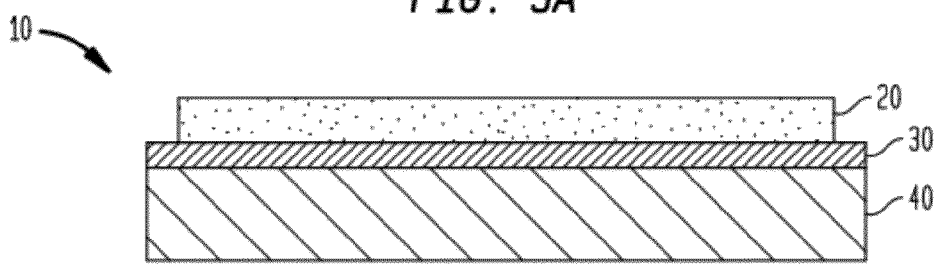
FIG. 5A is a side cross-sectional view of the solid substrate shown in FIG. 4 bonded to the structure of the bonded porous and intermediate layers shown in FIG. 3A.
Figure 5B:
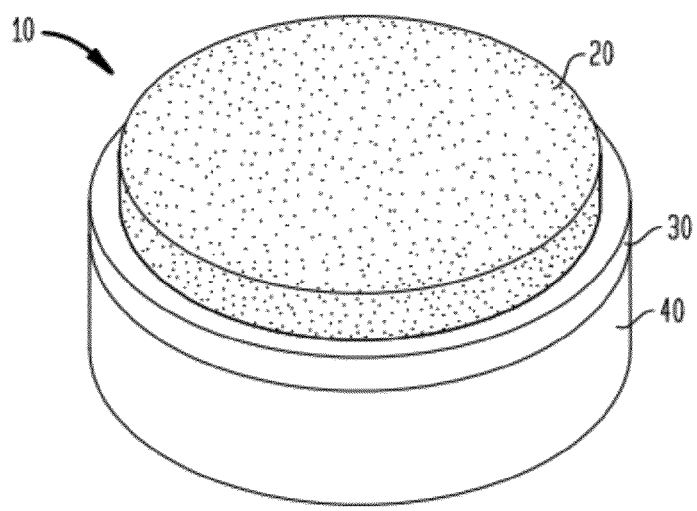
FIG. 5B is an isometric view of the bonded porous layer, intermediate layer and solid substrate shown in FIG. 5A.
Figure 5C:
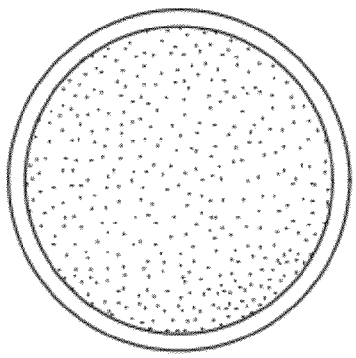
FIG. 5C is a top view of the bonded porous layer, intermediate layer and solid substrate shown in FIG. 5B.

FIGS. 5A and 5B shows inner surface 34 of intermediate layer 30 bonded to outer surface 42 of solid substrate 40. In the preferred embodiment, intermediate layer is bonded to solid substrate 40 by vacuum welding around the perimeters of intermediate layer 30 and solid substrate 40. After intermediate layer 30 and solid substrate 40 are bonded together via vacuum welding as shown in FIG. 5C a diffusion bond may be created between the intermediate layer and the solid substrate by hot isostatic pressing. Preferably, isostatic pressure is applied to the intermediate layer and solid substrate in order to create a diffusion bond between the bonded intermediate layer and solid substrate.

The vacuum sealing during welding preferably allows the interface between the intermediate layer 30 and solid substrate 40 to create a diffusion bond during the hot isostatic pressing process. If the space between intermediate layer 30 and solid substrate 40 is not sealed off with a vacuum weld, argon gas used during hot isostatic pressing may penetrate any space between intermediate layer 30 and solid substrate 40. As a result, the argon gas would likely push against both intermediate layer 30 and solid substrate 40 in opposite directions opposing a bond. With the vacuum weld, any space between intermediate layer 30 and solid substrate 40 is evacuated during welding, and therefore the argon gas during hot isostatic pressing pushes the intermediate layer 30 against solid substrate 40 creating a driving force for diffusion bonding.

Preferably, porosity 28 of porous layer 20 is substantially unaffected by the argon gas during hot isostatic pressing because the interconnected but open network of pores in porous layer 20 allows the gas to dissipate without crushing porous layer 20. The hot isostatic pressing process may serve to further consolidate the struts forming the porous structure without impacting the porosity 28 of porous layer 20. Additionally, because hot isostatic pressing is performed at moderate temperatures and high argon pressures, the bond between the intermediate layer 30 and solid substrate 40 occurs without significantly negatively affecting the mechanical properties of solid substrate 40.

Diffusion bonding by hot isostatic pressing requires fixturing only to hold a component such as orthopaedic implant and may be independent of size and/or geometry of the component being held. Furthermore, since the pressure used during traditional diffusion bonding is applied to the surface of the layers and is transferred across the interface, the pressures suitable for traditional diffusion bonding of porous metals are limited due to potential for crushing of the porous metal. Because the pressure in diffusion bonding by hot isostatic pressing is applied isostatically around the component and within and around the porous metal (within the pores), crushing of the porous metal is less likely and higher gas pressures can be used than permissible mechanical pressure.

Diffusion bonding using hot isostatic pressing can be used on components having complex geometries without the use of complex, expensive fixturing and load applications. Higher pressures will likely not crush the porous layer 20 during diffusion bonding because the pressure is applied directly to the interface of intermediate layers 30 and solid substrate 40 being bonded rather than transferring the load through porous layer 20.

Figure 6A:
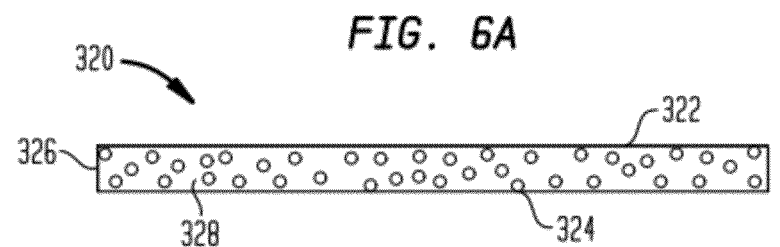
FIG. 6A is a side cross-sectional view of another embodiment of a porous layer.
Figure 6B:
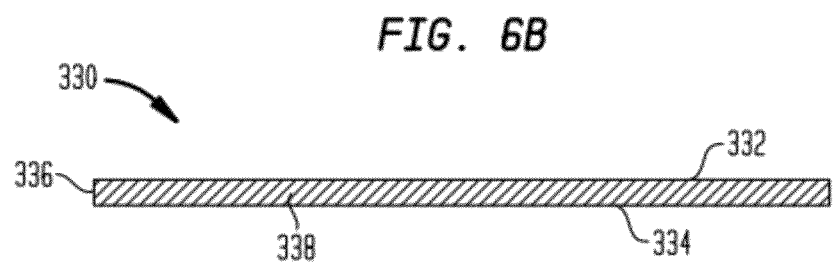
FIG. 6B is a side cross-sectional of one embodiment of an intermediate layer.
Figure 6C:
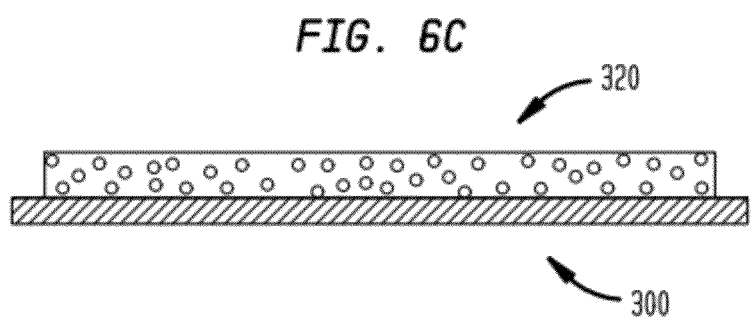
FIG. 6C is a side cross-sectional view of the porous layer shown in FIG. 6A bonded to the intermediate layer shown in FIG. 6B.
Figure 6D:
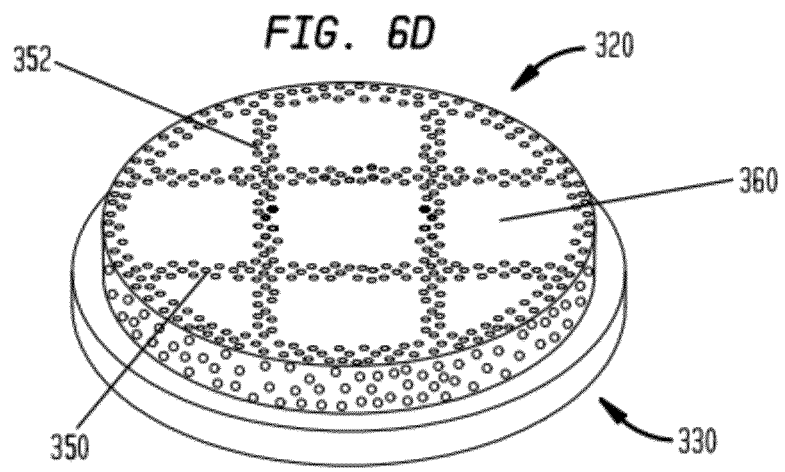
FIG. 6D is an isometric view of a structure having the bonded porous and intermediate layers shown in FIG. 6C.

FIG. 6A-6D show another embodiment of a porous layer 320 wherein a porosity 328 is formed in a particular configuration. Layer 320 may be manufactured by SLM or PM. Examples of SLM methods that may be used to manufacture layer 320 are disclosed in U.S. Pat. No. 7,537,664 and U.S. Pat. Pub. No. 2006/0147332, the disclosures of which are incorporated by reference herein in their entirety. Porous layer 320 has an outer surface 322, an inner surface 324 and a thickness 326. Porosity 328 of layer 320 is preferably formed by SLM or PM such that porosity 328 is formed in rows 350 and columns 352 as shown in FIG. 6D. Between rows 350 and columns 352 may be empty space or a solid substrate 360. The configuration of rows 350 and columns 352 may be altered in other embodiments, such that there are more or less rows 350 and columns 352 formed or the rows 350 and columns 352 are thinner or thicker. Further, the number of rows 350 and columns 352 do not have to be equal. Further still, other embodiments may only include rows 350 or may instead only include columns 352.

FIG. 6B shows another embodiment of an intermediate layer 330 having an outer surface 332, an inner surface 334, a thickness 336 and a porosity 338. As shown in FIG. 6C, inner surface 324 of porous layer 320 is bonded to outer surface 332 of an intermediate layer 330. An implant 300 may be manufactured in the same manner as implant device 10 is manufactured. The present embodiment differs from implant device 10 in the exemplary structure of porous layer 320.

Figure 7A:
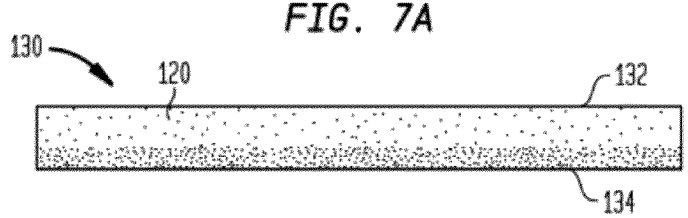
FIG. 7A is a side cross-sectional view of a layer having a porous outer surface and a substantially non-porous inner surface.
Figure 7B:
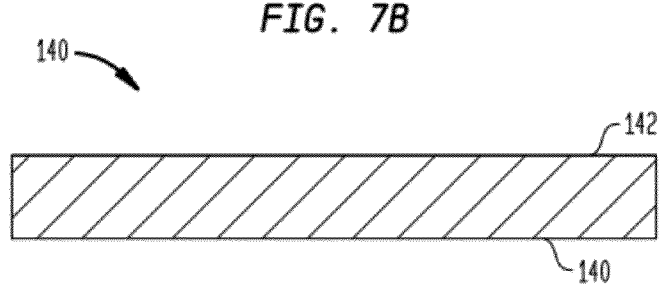
FIG. 7B is a side cross-sectional view of a solid substrate.
Figure 7C:
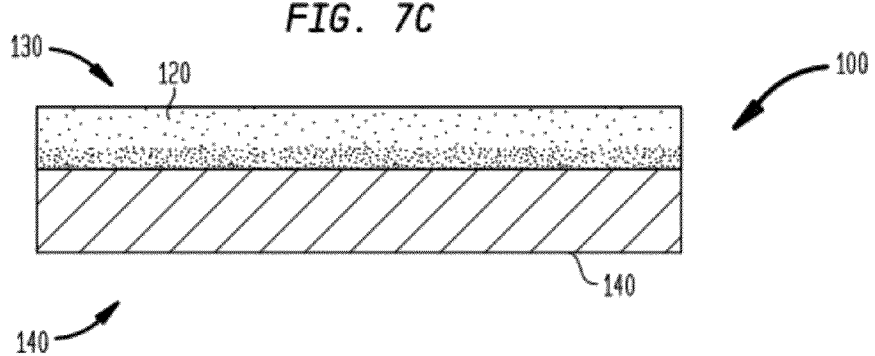
FIG. 7C is a side cross-sectional view of the layer shown in FIG. 7A bonded to the solid substrate shown in FIG. 7B.

FIGS. 7A-7C show another method of manufacturing an implant device 100 having a porous outer surface. The method includes providing a layer 130. A porous layer 120 is created on the surface of layer 130 by selective melting using either a laser or electron beam. The method includes providing a solid substrate 140 having an outer surface 142 and an inner surface 140. While solid substrate 140 is shown having a plate-like structure, solid substrate 140 is preferably in the form of an orthopedic implant device such as a femoral, tibial, or acetabular implant, for example. The method further includes bonding layer 130 to outer surface 142 of solid substrate 140 using vacuum welding around the periphery such that the formed porous layer 120 forms at least a portion of the outer surface of the orthopaedic implant device. Preferably, a diffusion bond is subsequently created between the bonded solid layer 130 and the solid substrate 140 by hot isostatic pressing.

In another embodiment, porous layer 120 may be created from the outer surface 132 of solid layer 130 by selectively melting a portion of the outer surface 132 in order to create pores in outer surface 132 such that a porous layer 120 is formed on outer surface 132 of solid layer 130.

Figure 8A:
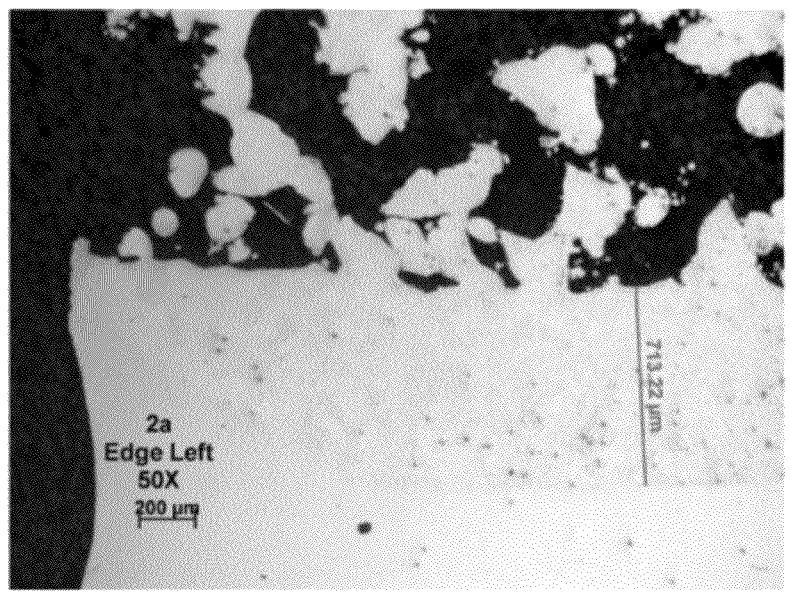
FIGS. 8A and 8B are light microscope images taken at 50 times magnification showing examples of diffusion bonds for the structure shown in FIG. 5D.
Figure 8B:
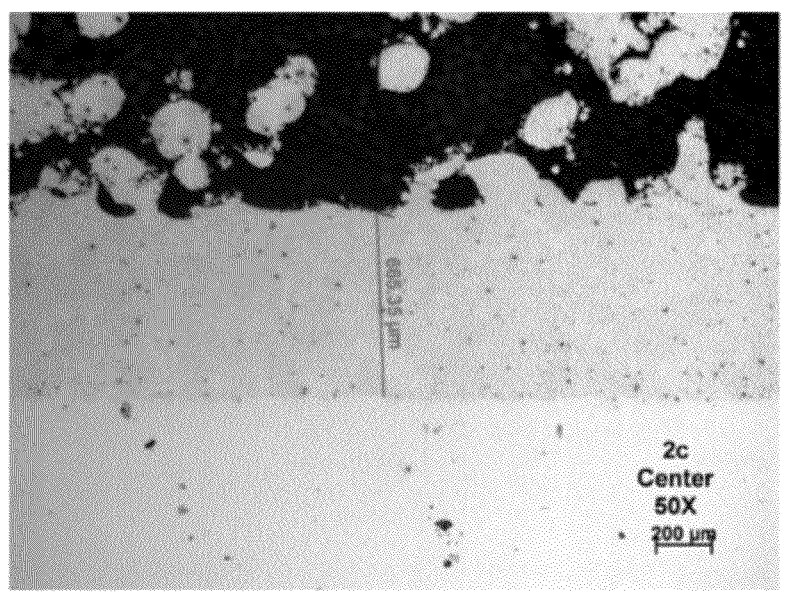

FIGS. 8A and 8B are examples of cross-sections of satisfactory diffusion bonds between the either the bonded intermediate layer 30 and solid substrate 40 as shown in FIGS. 5A-5D, for example, or the solid layer 130 and solid substrate 140 as shown in FIG. 7C, for example. There is good metallurgical bonding shown in the cross-sections.

Figure 9:
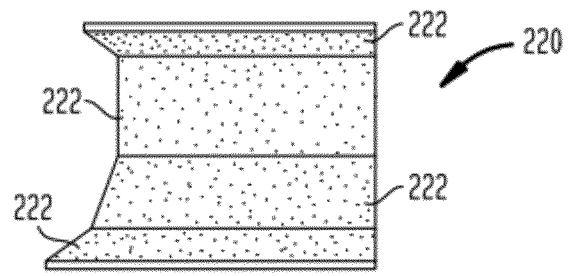
FIG. 9 is a plan view of bent porous layer.
Figure 10A:
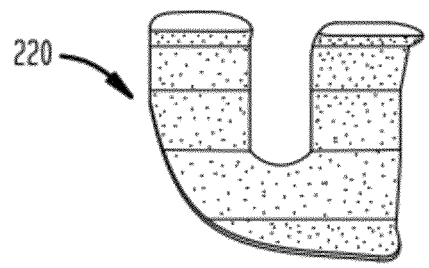
FIG. 10A is a plan view of a porous layer having the configuration of a knee femoral implant.
Figure 10B:
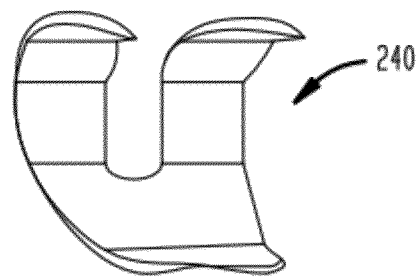
FIG. 10B is a plan view of a base layer having the configuration of a femoral implant.
Figure 10C:
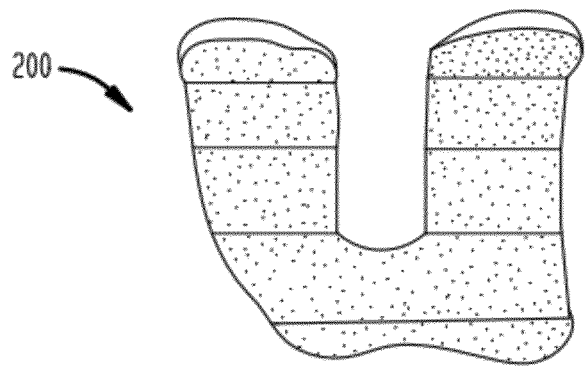
FIG. 10C is a plan view of the porous layer shown in FIG. 10A bonded to the base layer shown in FIG. 10B.
Figure 10D:
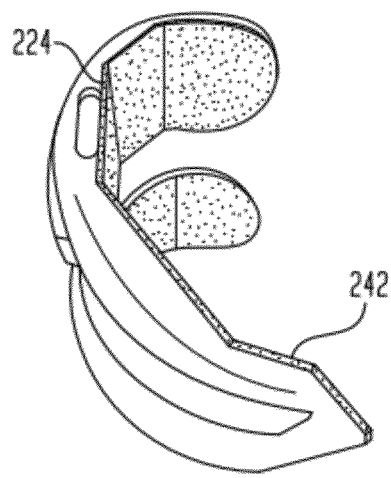
FIG. 10D is a perspective view of the bonded porous and base layers shown in FIG. 10C.

A porous layer 220 having a plurality of angled or bent portions 222 is shown in FIG. 9. SLM or PM may be used in order to manufacture porous layer 220. Porous layer 220 may be machined into the form of an inner surface for a femoral component as shown in FIG. 10A. Alternatively, SLM or PM may be used to manufacture a porous layer having the shape of a femoral component as shown in FIG. 10A. FIG. 10B shows a base layer 240 having the configuration of a femoral implant. FIGS. 10C and 10D show an inner surface 224 of porous layer 220 bonded to outer surface 242 of base layer 240 to create a femoral implant 200 having a porous surface on at least a portion of the outer surface thereof. Porous layer 220 is preferably bonded to base layer 240 by cold isostatic pressing.

Figure 11:
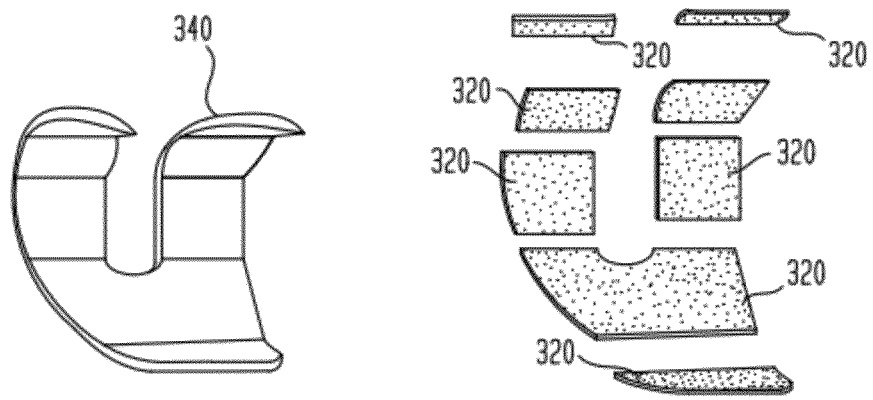
FIG. 11 is an exploded view of the base layer shown in FIGS. 10B and 8 as separate porous pads.

In another embodiment, separate porous layers 320 may be bonded to certain areas of a base layer 340 as shown in FIG. 11. The inner surface of a femoral component has five different angled surfaces representing the anterior, anterior chamfer, distal, posterior chamfer, and posterior surfaces. Because three of these surfaces are on separate condyles, namely the lateral and medial condyles, there are a total of eight separate surfaces on a femoral component that separate porous layers may be bonded to. Depending on the surgical need, a porous layer may be bonded to one or more of the eight separate surfaces.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, the present invention may be applied to hip systems as well.

The invention claimed is:

1. A method of manufacturing an orthopaedic implant device having a porous outer surface comprising:
   providing a solid layer having an outer surface and an inner surface, the inner surface having a perimeter;
   creating a porous layer having a porosity on the outer surface of the solid layer by selective melting;
   providing a solid substrate in the form of an orthopedic implant device having an outer surface and an inner surface, the outer surface having a perimeter;
   bonding the inner surface of the solid layer to the outer surface of the solid substrate by welding in a vacuum at an interface about the perimeters of the solid layer and solid substrate to create an initial bond about the interface such that the porous layer forms at least a portion of the outer surface of the orthopaedic implant device, the initial bond sealing the interface wherein no gas can subsequently pass through the interface; and
   creating a diffusion bond between the bonded solid layer and the solid substrate by hot isostatic pressing after the initial bond is created in order to maintain the porosity of the porous layer.

2. The method of claim 1, where the selective melting is performed with a laser.

3. The method of claim 1, wherein the solid layer consists of titanium.

4. The method of claim 1, wherein the solid layer is a titanium alloy.

5. The method of claim 1, wherein the solid substrate consists of titanium.

6. The method of claim 1, wherein the solid substrate is a titanium alloy.

7. The method of claim 6, wherein the solid substrate is substantially non-porous.

8. A method of manufacturing an orthopaedic implant device having a porous outer surface comprising:
   creating by selective melting a layer having a porous outer surface having a porosity and a substantially non-porous inner surface, the inner surface having a perimeter;
   providing a solid substrate in the form of an orthopedic implant device having an outer surface and an inner surface, the outer surface having a perimeter;
   bonding the inner surface of the layer to the outer surface of the solid substrate by welding in a vacuum at an interface about the perimeters of the layer and the solid substrate to create an initial bond about the interface such that the porous outer surface of the layer forms at least a portion of the outer surface of the orthopaedic implant device, the initial bond sealing the interface wherein no gas can subsequently pass through the interface; and
   creating a diffusion bond between the bonded solid layer and the solid substrate by hot isostatic pressing after the initial bond is created in order to maintain the porosity of the porous outer surface of the layer.

9. The method of claim 8, where the selective melting is performed with a laser.

10. The method of claim 8, wherein the solid layer consists of titanium.

11. The method of claim 8, wherein the solid layer is a titanium alloy.

12. The method of claim 8, wherein the solid substrate consists of titanium.

13. The method of claim 8, wherein the solid substrate is a titanium alloy.

14. The method of claim 13, wherein the solid substrate is substantially non-porous.

* * * * *